(12) United States Patent
Cano et al.

(10) Patent No.: US 12,183,439 B2
(45) Date of Patent: Dec. 31, 2024

(54) PROCEDURE FOR THE GLOBAL UNIFIED REGISTRATION AND UNIVERSAL IDENTIFICATION OF DONORS

(71) Applicant: CONECTATE SOLUCIONES Y APLICACIONES S L, Soria (ES)

(72) Inventors: Nuria Sala Cano, Soria (ES); Fernando Latorre Lopez, Soria (ES)

(73) Assignee: CONECTATE SOLUCIONES Y APLICACIONES S L, Soria (ES)

( * ) Notice: Subject to any disclaimer, the term of this patent is extended or adjusted under 35 U.S.C. 154(b) by 517 days.

(21) Appl. No.: 17/178,966

(22) Filed: Feb. 18, 2021

(65) Prior Publication Data

US 2021/0174914 A1    Jun. 10, 2021

Related U.S. Application Data

(63) Continuation-in-part of application No. 15/580,880, filed as application No. PCT/ES2016/070428 on Jun. 7, 2016, now abandoned.

(30) Foreign Application Priority Data

Jun. 8, 2015    (ES) ............................ ES201530667U
Nov. 6, 2015    (ES) ............................... ES201531661

(51) Int. Cl.
*G16H 10/40*    (2018.01)
*G16H 10/60*    (2018.01)
(Continued)

(52) U.S. Cl.
CPC ............ *G16H 10/40* (2018.01); *G16H 10/60* (2018.01); *G16H 80/00* (2018.01); *H04L 9/0825* (2013.01); *H04L 9/3247* (2013.01)

(58) Field of Classification Search
CPC ...... G16H 10/40; G16H 10/60; H04L 9/0825; H04L 9/3247
See application file for complete search history.

(56) References Cited

U.S. PATENT DOCUMENTS 8,676,600 B2    3/2014    Case et al.
2003/0004751 A1 *    1/2003    Ng ......................... G16H 15/00
                                                                          705/2

(Continued)

FOREIGN PATENT DOCUMENTS

EP         2290571 A1        3/2011
WO    WO-2005097190 A2 *    10/2005    ........... C12N 5/0605
(Continued)

OTHER PUBLICATIONS

International Search Report for Application No. PCT/ES2016/070428 dated Sep. 19, 2016.
(Continued)

*Primary Examiner* — Sheetal R Paulson
(74) *Attorney, Agent, or Firm* — Norton Rose Fulbright Canada LLP; Maya Medeiros

(57) ABSTRACT

A procedure for the global unified registration and universal identification of donors is described. The method includes a creation of one or more donor profiles, relevant medical data profiles, and a public common donor identifier from an initial registration. The procedure further includes identifying the donor by a donation center through a personal and non-transferable code for access to the data, the public common donor identifier and the stored profiles. The procedure automatically updates donor's data, profiles, and donation history in a database accessible by different donation centers.

9 Claims, 2 Drawing Sheets

(51) Int. Cl.
G16H 80/00 (2018.01)
H04L 9/08 (2006.01)
H04L 9/32 (2006.01)

(56) References Cited

U.S. PATENT DOCUMENTS

| | | |
|---|---|---|
| 2004/0030578 A1 | 2/2004 | Cross et al. |
| 2007/0219826 A1* | 9/2007 | Brodsky ................ G16H 10/20 705/2 |
| 2012/0297255 A1 | 11/2012 | Case et al. |
| 2015/0310174 A1 | 10/2015 | Coudert et al. |
| 2016/0260002 A1 | 9/2016 | Hill et al. |

FOREIGN PATENT DOCUMENTS

| | | |
|---|---|---|
| WO | 2007014147 A2 | 2/2007 |
| WO | 2014090411 A2 | 6/2014 |
| WO | 2014186559 A2 | 11/2014 |
| WO | 2016198713 A1 | 12/2016 |

OTHER PUBLICATIONS

InteropEHRate, Unleashing Personal Health Data for Care and Resesarch: The InteropEHRate Approach, White Paper, Aug. 25, 2021.
Examination Report dated Jan. 29, 2021 issued on Indian Patent Application No. 201717044627.
PCT, Written Opinion and International Search Report of International Application No. PCT/EP2022/054164, mailing date Jun. 1, 2022.

* cited by examiner

PROCEDURE FOR THE GLOBAL UNIFIED REGISTRATION AND UNIVERSAL IDENTIFICATION OF DONORS

CROSS-REFERENCE TO RELATED APPLICATIONS

This application is a Continuation-in-Part or pending U.S. patent Ser. No. 15/580,880 filed on May 9, 2018, which is a U.S. National Stage under 35 U.S.C. 371 patent application, claiming priority to Serial No. PCT/ES2016/070428, filed on 7 Jun. 2016, which claims priority of ES U201530667, filed on 8 Jun. 2015 and ES P201531611, filed on 6 Nov. 2015, the entirety of each are hereby fully incorporated herein by reference.

TECHNICAL FIELD

The field of application of the present invention is the health sector, particularly in the area of blood donation collection centers, encompassing at the same time, data management systems.

BACKGROUND

Blood is a type of connective tissue, it has an extracellular matrix called plasma, with red blood cells, white blood cells, and platelets floating in it. Currently, a same individual can have several donor cards and local donor identifiers in different donation centers of distinct organizations and territories, for example when using the ISBT Donor Identification Number (data structure 019) where the Facility Identification Number or FIN comprises the first five characters of the 21-character Donor Identification Number. When donating a self-exclusion donation questionnaire regarding the individual's health and previous diseases must be fulfilled, but there isn't an automatic way to know and to verify data of a same individual in distinct healthcare or donation centers (public and/or private) in one or more organizations with different computer systems and databases in one or several territories.

There is currently no known cross-border data access and identification system for donor information through distinct donation organizations, different electronic devices and computer systems using distinctive software applications and database systems, which would allow to improve healthcare and donation ecosystems, the security of both donors and potential recipients and saving costs, for example by not allowing individuals previously excluded in other donation facilities or with some detected diseases to donate (saving in costs of extraction, handling, analysis, administration and destruction of biological products and avoiding unnecessary risks to potential recipients of biological products extracted or obtained from the donation) and not allowing to donate if the maximum number of donations in the last 365 days has been reached or minimum time between donations has not been passed according to the specific legislation of a territory for the security of donors.

The relative information of donors can become very extensive and varied; from the particularities of each donor, relative to the blood group, age, donations made (e.g. in different centers/organizations from distinct territories or countries), etc., to the possible incidents or circumstances that may prevent an individual either becoming a donor or modify their chances of continuing to be a donor temporarily or definitively, such as a trip to a place at risk of endemic diseases, relevant disease detected, medical interventions, recent medical or dental treatments, medications, etc., as well as other conditions.

The Continuous Care Document (CCD) is an implementation of the HL7 Clinical Document Architecture but only for the United States of America. CCD fosters interoperability of clinical data in the U.S. by allowing physicians to send electronic medical information to other providers without loss of meaning and enabling improvement of patient care. It is an XML-based standard and was recognized in 2008 by the U.S. Secretary of Health and Human Services and has been named in U.S. Regulations for exchange of clinical information. The Trillium Bridge project (2013-2015) compared patient summary standards and specification in Europe and the United. Reflecting on its results, Trillium-II continues the efforts of Trillium Bridge to achieve progress on its recommended actions and advance adoption of the International Patient Summary (IPS) supported by broadly and consistently implemented standards. The CEN project 'International Patient Summary' (funded by EU, reference: Specific Agreement CEN/2015-16) aims to support 1) the European participation in this global standardization activity and 2) the development of a European standard on Patient Summaries, based on the global standardization work. The technical specification for implementation of the Patient Summary provides guidance on how to make it work in real life, with a focus on the HL7 International Patient Summary standard in both HL7 CDA and HL7 FHIR formats. An International Patient Summary (IPS) document is an electronic health record extract containing essential healthcare information about a subject of care. As specified in EN 17269 and ISO/DIS 27269, it is designed for supporting the use case scenario for 'unplanned, cross border care', but it is not limited to it. It is intended to be international, i.e., to provide generic solutions for global application beyond a particular region or country. IPS was approved in 2018 by the European Committee for Standardization (CEN).

Directive 2011/24/EU on the right of patients in cross-border healthcare, article 4.2.f establishes in order to ensure continuity of care, patients who have received treatment are entitled to a written or electronic medical record of such treatment, and access to at least a copy of this record. Also, European General Data Protection Regulation or GDPR, article 20, establishes the right to data portability: The data subject shall have the right to receive the personal data concerning him or her, which he or she has provided to a controller, in a structured, commonly used and machine-readable format and have the right to transmit those data to another controller without hindrance from the controller to which the personal data have been provided, where the processing is based on consent and the processing is carried out by automated means.

The United States Core Data for Interoperability (USCDI) regulation was approved in 2020 and requires Electronic Health Record (EHR) systems to enable access to their software via FHIR-based APIs (Application Programming Interface), so that patients can use the APIs to be able to electronically access all of their electronic health information (EHI), structured and/or unstructured, at no cost. So regulations allow people to receive/download their health information automatically in an electronic way, which allow people to unify health information and identifiers from different sources and to share their data in their own, like this invention proposes for cross border data portability and data resilience. People should have remote access to and they should have the right to have a copy of their medical records (FHIR API and FHIR resources) for cross-border healthcare, in a structured, commonly used and machine-readable format (IPS/FHIR formats as were established by CEN and USCDI) and also people have the right to transmit those data to another controller without hindrance from the controller to which the personal data have been provided, in a secure and electronic way. These regulations are applicable to receive and to share the health information currently available in distinct healthcare systems and also for new health information generated by a healthcare professional in a public or private healthcare service (laboratories, hospitals, employee liability insurances, etc.).

In other hand, HL7 Foundation establishes some JSON Canonization Rules for JSON (JavaScript Object Notation) representation of resources, e.g.: Resources and/or Bundles may be digitally signed, Order properties alphabetically, The narrative (Resource.text) is omitted prior to signing (deletion of Resource.text), Resource.meta element is removed. This makes the signature robust as the content is moved from server to server, and these canonicalization methods allow system the flexibility to sign the various portions of the resource that matter for the workflow the signature serves. In this way, the proposed invention can incorporate an IPS document in the code generated, and the IPS document can be digitally signed. Removing text reduces size, and the IPS document is also suitable to be both encrypted and compressed to be transmitted within a QR or NFC code, for example, and also is suitable to be transmitted via Bluetooth, without requiring network connection in any case to internet or to a server, allowing data portability and resilience.

Also in this matter, Hyperledger Aries RFC 0434 Out-of-Band Protocol was proposed in 2020 to deliver out-of-band DIDComm messages using JSON within this protocol, and encodes the messages for public key exchange to establish a secure connection. The Out-of-band messages can be encoded and transferred via any method that can send text, including an email, SMS, posting on a website, QR Code or others. In this way, message transmission is transport-agnostic. That is, the messages can flow over any combination of HTTP, Bluetooth, NFC, email, AMPRNet (TCP/IP over ham radio), snail mail, sneakernet, intermediaries, or future protocols. Messages are JSON ([RFC8259]) and the messages are serialized and encrypted in a standard way for transport.

DIDCommunications (DIDComm) is a set of tools to allow horizontal (or at least, power-neutral) and bidirectional channels of communication between two entities that know each other's DIDs and nothing else. DID (Decentralized Identifiers) are two things: an identifier and a JSON document associated to that identifier (a decentralized document identifier). The standard DID specification of the World Wide Web consortium W3C establish the DID document as a repository of public verifiable cryptography information, so asymmetric public encryption and signing keys are stored in the DID document and are used to be exchanged with others to stablish secure communications (DIDCommunications), to verify digital signatures and to exchange data (e.g.: Hyperledger Aries DIDComm Exchange protocol) both in online and offline modes (Hyperledger Aries Out-Of-Band protocol) through a secure connection. So the DID Document acts as the repository of the public verifiable cryptography information of an entity and it can be used to store and to exchange the public verifiable cryptography information of people and organizations, such as donors, practitioners and healthcare and donation services.

DIDs differ from public keys in that DIDs are persistent, i.e. a public key has to be changed if the private key is stolen/lost or the cryptographic scheme of the public key is no longer considered safe. This is not the case with DIDs, they can remain unchanged even when the associated cryptographic material changes. Moreover, a DID can have multiple keys and any of its keys can be rotated. The DID Document specifies the public keys of the subject, the authentication mechanisms usable by the subject, authorizations the subject has given to others, service endpoints to communicate with the subject, etc., for all properties that can be put in the DID Document, specified by the W3C.

The object of the present invention is therefore to avoid current problems of data isolation, data atomization, multiple identifiers non reusable in other organizations and/or territories, and health data portability problems by developing a unified personal and non-transferable registration code and a universal identification of the donors that can be utilized in a quick and practical manner by all of the centers of one or more territories, whether the donor has ever visited that center or another, for cross border identification across distinct donation facilities, different electronic devices and computer systems using distinct software applications and database systems.

Up to this point there hasn't been a common system or cross-border of obtaining information of donors on the part of the centers and hospitals that perform the collection of donations (of blood or from other tissues or cells). Since in practice, different database management systems and software solutions are used, and the data are also isolated in different corporations, regions or states, whereupon, though some donors are provided with a donor card from a particular center with little information only for identification in that center (donor number for that center, name, surname and blood group), each donation center independently maintains the information on their donors (donations made, donation dates, etc.) segregated from other regions, states or corporations.

The objective of the herein invention is therefore to avoid said inconvenience by developing a unified global registration of donors for all territories through a code of personal and non-transferable identification. This global and unified donor register allows the use, in a universal, quick and practical way, by any center regardless of territory (region, state, . . . ), database management system or software solution for the identification of donors of any kind and to obtain in any center a unified history of donation and possible exclusions from the donation, whether they have previously donated or if it is the first time they are presenting to donate. Also allows donors to carry their health data and to share this data at any center, regardless the territory or organization.

There are two general classes of barcodes: one-dimensional (1D or linear) and two-dimensional (2D). The Data Matrix barcode (ISO/IEC 16022) is a high-density, two-dimensional (2D) symbology that encodes text, numbers, files and actual data bytes. A QR code is a type of matrix barcode and allows to encode information in bits. It is the most popular 2D barcode type for document Information. A QR code uses four standardized encoding modes (numeric, alphanumeric, byte/binary, and kanji) to store data efficiently; extensions may also be used. In byte mode, the data string consists of the mode indicator, the character count indicator, and then the raw bytes. The maximum storage in a QR code is 4296 alphanumeric characters or 2953 bytes in binary data; the binary data can contain one or several files and the files can be compressed in zip or other formats (e.g.:

to reduce the size of JSON files up to 8 times their original size); the binary data can also be digitally signed and encrypted before being compressed, or can be signed after the compression, using an encryption and signing keys, to protect and to verify the authenticity of the data contained in the QR code.

A 2D barcode doesn't just encode alphanumeric information as 1D barcodes. 2D barcodes can also contain images, website addresses, voice, and other types of binary data, and it allows to store and carry different types of objects encapsulated in several records (as NFC does, but not all mobile phones have NFC connectivity, nor can NFC be printed, for example). In byte mode, the data consists of the mode indicator, the character count indicator, and then the raw bytes. The binary data encoded in the QR code can be any type of binary data (e.g. XML, JSON, IPS, digitally signed, encrypted, compressed, a DID Document, etc.) and allows to maximize the amount of information stored and to protect the information stored. This means that the information can be used whether there is a connection to a database or not and files can travel, stored into an item labeled with a 2D barcode. The QR code can be generated and scanned with an image sensor such as a camera installed in an electronic device to convert the QR code to binary data and to get the information it contains encoded. No network connection is required to generate/read and to encode/decode the data in a QR code, allowing data portability and resilience (e.g. if network connection has been down in case of natural disasters, virus attacks or terrorism).

As an example, some medical data can be marked as relevant by the practitioners or by the donor themselves and this data can be stored as private data and encoded and stored as encrypted binary data through the binary encoding in the QR code; also the binary information contained in the identification code can be digitally signed by using distinct symmetric or asymmetric algorithms, e.g. Advanced Encryption Standard (AES), Rivest-Shamir-Adleman (RSA), Diffie-Hellman, Elliptic Curve Cryptography (ECC), Digital Signature Algorithm (DSA), etc. An explanation of how the information can be stored, protected (encrypted) and signed into a 2D matrix barcode in QR format is provided below:

A QR code is a type of matrix barcode and allows to encode information in bits. In binary encoding, the binary data can contain one or several files and the files can be compressed in zip or other formats (e.g.: to reduce the size of JSON files up to 8 times their original size); the binary data can also be digitally signed and encrypted before being compressed, or can be signed after the compression, using an encryption and signing keys, to protect and to verify the authenticity of the data contained in the QR code.

Digital signature is a mathematical scheme for demonstrating the authenticity of a digital message or document. Digital signatures are used in the cases where it is important to detect forgery or tampering. A digital signature is an authentication mechanism that enables the creator of a message to attach a code that acts as a signature. A digital signature scheme typically consists of three algorithms: 1) A key generation algorithm that selects a private key uniformly at random. The algorithm outputs the private key and a corresponding public key. 2) A signing algorithm that, given a message and a private key, produces a signature. 3) A signature verifying algorithm that, given a message, public key and a signature, either accepts or rejects the message's claim to authenticity.

As above mentioned, the binary information can be files, such as an IPS document in FHIR format or other FHIR resources in XML (Hypertext Markup Language) or JSON (also ZIP files containing a IPS document or FHIR resources to increase the storage capacity, among others types); the files optionally can be digitally signed into the 2D matrix code with a signing key created by the donor or generated by other way such as by a biometric signal by a software application, or can be signed capturing biometric information of the donor during a signing process by a software application. These files in turn can be optionally encrypted by means of an encryption key through a software application, so that the binary information can be stored and carried safely in an efficient and resilient way within a matrix barcode, such as a QR code. Symmetric and Asymmetric Encryption methods can be used and using compressed files (such as ZIP among others possible) the information can also be protected and encrypted within the file by setting a password as a seed for generating the encryption key.

U.S. Pat. Pub. No. 2007/0219826 to Brodsky et al. discloses a method to decrease the use of paperwork and forms by using electronic workstations to enter donor and donation information, to reduce the number of staff necessary to run the center. It discloses a method to read bar-coded labels on a tube to determine the content of the tube, to digitalize the donor information in a local database (personal data, photo, digitized signature, questions), an internal communication network in the center to communicate data between the local nodes or workstations of the practitioners and the local server of that center (exclusively for the staff). It cited unique donor information may include a local system-assigned unique donor ID for a concrete network and additional personal data of the donor (name, date of birth, social security number, driver's license number) and the method can use RFID, magnetic strips, biometrics identifiers such us fingerprints to identify the donor in the local network, but it does not describe how to use a cross border public common identifier for multiple networks and database systems. Also, that method it is not intended to unify health data and identifiers, neither for data portability, cross border care or data resilience. As example, if a donor is excluded for donating, the method describes that a printed letter explaining why the donor is not eligible for the donation is given to donor, but it does not disclose how the donor can have the electronic data generated in the center on their mobile phone in an automatic way, how other centers can know or access the updated data of the donor in the local database, or how the local network can share relevant data with other centers automatically. Also describes a review module for questions made to the donor in that center, a process progress status to track the donation procedure, and a donation correlation management module for tracking donations registered in the local network and documenting health information related to the donor, but it does not disclose a method to verify data carried by the donor from other centers, how to access data from other centers or how other centers, databases and computer systems can know the result of a distinct donation process or relevant health data of the donor in the local network and database.

U.S. Pat. Pub. No. 2016/0260002 to Hill et al. discloses an access control for segmented data in machine-readable identifiers using several cryptographic keys for encrypt different portions of data and a unique identifier that identifies a device authorized to access the encrypted data, but it is not intended and does not disclose how to unify different healthcare identifiers and health data from distinct healthcare systems. It cited the cryptography key may be set as a date of birth, social security number, or other constant that may not be widespread or publicly available, so is not intended to be used in the same way as the present invention proposes for the universal identification of donors through a public common donor identifier which can be associated to local donor identifiers (for an individual, not for devices)

U.S. Pat. Pub. No. 2004/0030578 to Cross et al. discloses a method and system for comparing the patient data and the review criteria to determine if the patient data should be routed for review. It reviews changes in the value data of several tests to trigger a review of the test performed. This method and system is not intended for cross border care and it does not disclose how data in the local system can be accessed from other systems to check the veracity of the data of a patient (not for reviewing historical values of several tests) or how the local system can check the veracity of the data of a patient which has been generated in other systems.

U.S. Pat. No. 8,676,600 to Case et al. discloses a method for displaying a graphical representation of a donor's donation. It includes that a center can send events to donors and that the donor can know where to make a donation in that center, based on location, preference, eligibility, etc. This method is not intended for cross-border care to find out the locations of different centers, whether the individual is a donor in a specific center or not, nor is it not intended to automatically detecting the presence of a donor in areas of endemic diseases.

U.S. Pat. No. 10,872,307 to Mickles et al. discloses systems and methods for managing inventories of blood components, to improve the predictability, efficiency, and/or automation of blood component supply chains. It includes a Donor Profile Module and the donor profile is a donor-specific data space within the memory of the management system, which is accessible using a unique identifier. The blood component supply chain management system is owned, operated, or managed by, or otherwise tailored to, an individual blood center and/or health care facility. The system may enable a blood center to track its own inventory as well as the inventory of its customers and recruit, schedule, and manage communications and relationships with donors and potential donors. Additionally or alternatively, the system may enable health care facilities to track their own respective inventories. In some embodiments, each health care facility utilizing the system may additionally be able to view the inventory levels of the system-affiliated blood center. The management system may be accessible via a web-based interface or application interface to enable review of historical collections and the characteristics of scheduled donors. So, the donor identifier is a system-specific identifier for an individual blood center and/or health care facility, and the above invention is not intended to be used for cross border identification or to unify distinct health identifiers and health data from distinct databases and computer systems for cross border care and data portability.

Above mentioned patents do not are intended to unify health identifiers and data from distinct centers, neither for cross-border care, data interoperability, security and data resilience. Specifically, what the invention proposes, as indicated above, is a procedure for the registration and identification of donors developed with the aim of achieving the unification of the registration system and of the identification of the donors in distinct isolated donation facilities with different database systems (for example in a same territory or in several territories) and facilitate the exchange of information related to them even in offline mode, to access both the main donor profile, the common public identifier of the donor and other data contained in the main donor profile or in other profiles of the donor, such as the local donor identifier at a specific donation center or facility (if the donor also has a local donor identifier at that facility) and other data relevant to the donation procedure such as medical data, the unified donor history, and also allows knowledge of donor exclusion for any reason whether that be total exclusion or if a donor is excluded temporarily and can return to donating after a period of time, regardless of which center or place the identification of the individual was done. It allows, for example, the unification of records of the same individual stored in the different data management systems by the different existing software solutions, by means of the association of the identifier granted to the individual for a specific center with the public common donor identifier proposed by this invention, to be used by the different centers and associated with the unified identification code of the individual, which allows the increase in traceability of individuals and their donations in a global manner for any software solution and universal for any center.

The invention, intended for patent, is aimed at the universal traceability of individuals for any kind of donation in any territory, computer system and database installation. As mentioned above, in practice there is a break-down and disintegration of data between different systems of database management, different software solutions for the management of the donation, not only for blood donation but also for other types of donation, which are also isolated from each other depending on the territories. The current ecosystem derives, therefore, from analytical duplication problems in different centers and unnecessary expenses if it had been previously detected that an individual could not donate for any reason, unsafety in the donation made and possible health problems in the donor by failing to check their donation history (previous donations in the same year, exclusions from donation, adverse reactions occurrence on previous occasions . . . ). Nor does it allow the awareness of other data or events relevant to the donation from other medical centers (allergies, prescribed medications, severe health disorders, surgical, dental, or punctures of any kind, etc.).

Currently, the donor's blood is traced to the recipient (product traceability). In addition, if the donor develops a serious non-infectious disease (cancer, autoimmune diseases, etc.), the recipients are monitored only if the donor is diagnosed at the same donation center in which the donation was made or whether the donor them self advises the center of donation of their circumstance after donation has occurred. The National Donor Deferral Registry (NDDR) is a database of permanently deferred source plasma donors but only in North America. It is a voluntary, self-regulating initiative taken by the source plasma collection industry to protect donated plasma receptors from receiving plasma infected with hepatitis or HIV, where people diagnosed with any of these diseases in these plasma donation centers are excluded from the donation of plasma there, and donors have the possibility to ask to be added to this register if they have been diagnosed in other centers other than plasma donation centers.

Although there is no evidence that some diseases such as cancer can be transmitted by blood, neither is the form of generation or development of cancer in an organism known with certainty. It is not known, therefore, whether metastasis (dissemination of cancerous cells through the blood or lymphatic system within the same organism) can pass from one individual to another during the process of a donation. The invention that is intended to be patented allows for cooperation between the different health and donation centers in order to create alerts, study and follow-up on donations, blood transfusions and the development of non-infectious serious diseases of which the transmission mechanism is not known.

There is therefore no universal system to let know if an individual diagnosed with a serious non-infectious disease, such as cancer or autoimmune diseases, is a donor in any donation center. It is also not possible to bring to the attention of a donation center in any territory by automatic alert of serious non-infectious illness detected in an individual who is already a donor in another center to enable protocols and exclude them from the donation. There is also no possibility of excluding from donation an individual who has been detected with a serious illness of any kind, in an automatic and global manner for any donation center regardless if the individual has donated in any of them or not.

On the other hand, there also does not currently exist the possibility of generating an alert from a medical center that diagnose a serious non-infectious disease (such as those cited previously) in a patient who has been a recipient of a single or several donations at any point to the center or centers of origin of those, which prevents studies of traceability from the individuals originating from these donations to the rest of donations made by these donors and to the rest of the individuals receiving them, since there is no system that allows communication and global cooperation between medical centers and donation centers in any territory and for any type of donation through a unified and universal donor registry as proposed by this invention.

An example of the use of this invention would be the one described below. As a result of a global donor unification registry of any kind, studies and follow-ups could be carried out that through the analysis of Big Data and artificial intelligence would allow the study and analysis of cancer cases in donors of any kind and receivers of any type of donation or blood product that have taken place in any territory. For example, a study could establish a common link between different recipients of donations or blood products (these individuals denominated as R1, R2 and R3) who had been diagnosed with cancer sometime after receiving them, with a certain donor that would also have been diagnosed with cancer in a medical center after having made different donations over time in different regions.

Through this study, cited as an example, it could be established that several donors (denominated D1, D2, D3, D4, D5 and D6) have participated in the donations that have been used for these three recipients and furthermore, that donor D1 has also been diagnosed with cancer after they had donated in various territories. Thus allowing, on the one hand, the study of these cases in a transversal and in-depth manner in order to establish additional measures or protocols based on the results obtained, and on the other hand, follow up on the rest of donations made by donor D1 and study the appearance or not of this type of disease in all the recipients involved.

As a reference to the current state of the art, it should be well-noted that, although different types of identification systems, the existence of any that allows to unify local identifiers of donors from different donation facilities in a unique identification code for the same individual and to carry and share medical data in a secure and resilient way, even without network connection to internet or to the local computer system of the donation facility, is unknown at least on behalf of the applicant.

SUMMARY

The invention, as expressed in the title of the present specification, refers to a unified registration procedure and identification of donors, which has advantages and characteristics, which will be described in detail below, which involve an improvement of the current state of the technique. The procedure means a particular method to carry out the steps of both phases for the unified registration and for the universal identification of donors.

The object of the present invention rests, in particular, in a procedure whose purpose is to achieve the unification of the registration and identification of donors (blood donors among others such as donors of plasma, platelets, red blood cells), such as the donors registered in all the centers of certain territories, in order to facilitate the exchange of information regarding said donors and avoid the atomization and disintegration of data, saving resources to the donation centers and increasing healthcare security (e.g. saving costs in personnel, analytics, material and destruction of biological products by not allowing a donor previously excluded in one center to donate in another center). Said procedure consisting in generating, by the donor themselves, through a software application with an electronic device (mobile, tablet, . . . ), or by the centers through a software application for the practitioners and/or by the computer system of each center, a unique and non-transferable identification code containing a main donor profile with data from the donor and associated with an unique and universal public common donor identifier (for example a random identifier for cross border identification over distinct database systems) and distinct local donor identifiers from different donation facilities, which is deposited and stored as a digital record both in a software application or the donor (installed in an electronic device) and in a common database of a computer system accessible by different electronic devices and computer systems of distinct donors, practitioners and centers.

BRIEF DESCRIPTION OF THE DRAWINGS

To complement the description that is being made and in order to provide a better understanding of the characteristics of the invention, the present description is accompanied, as an integral part of the same, by a plan in which the following has been represented with an illustrative and non-limiting character.

DETAILED DESCRIPTION OF THE INVENTION

Figure 1:
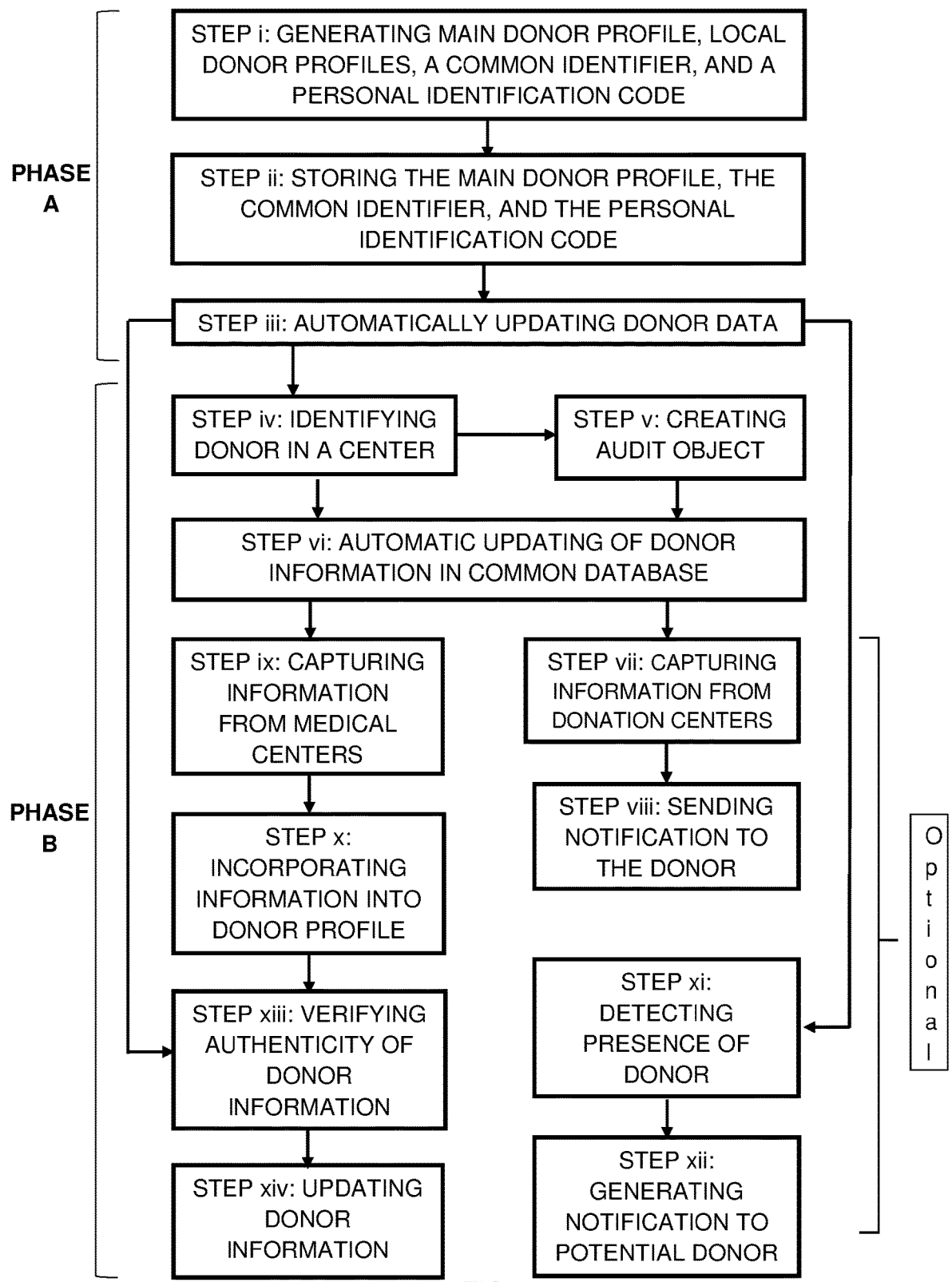
FIG. 1 is a block diagram flow chart illustrating the operation of the unified registry and the universal identification of donors, according to the invention.
Figure 2:
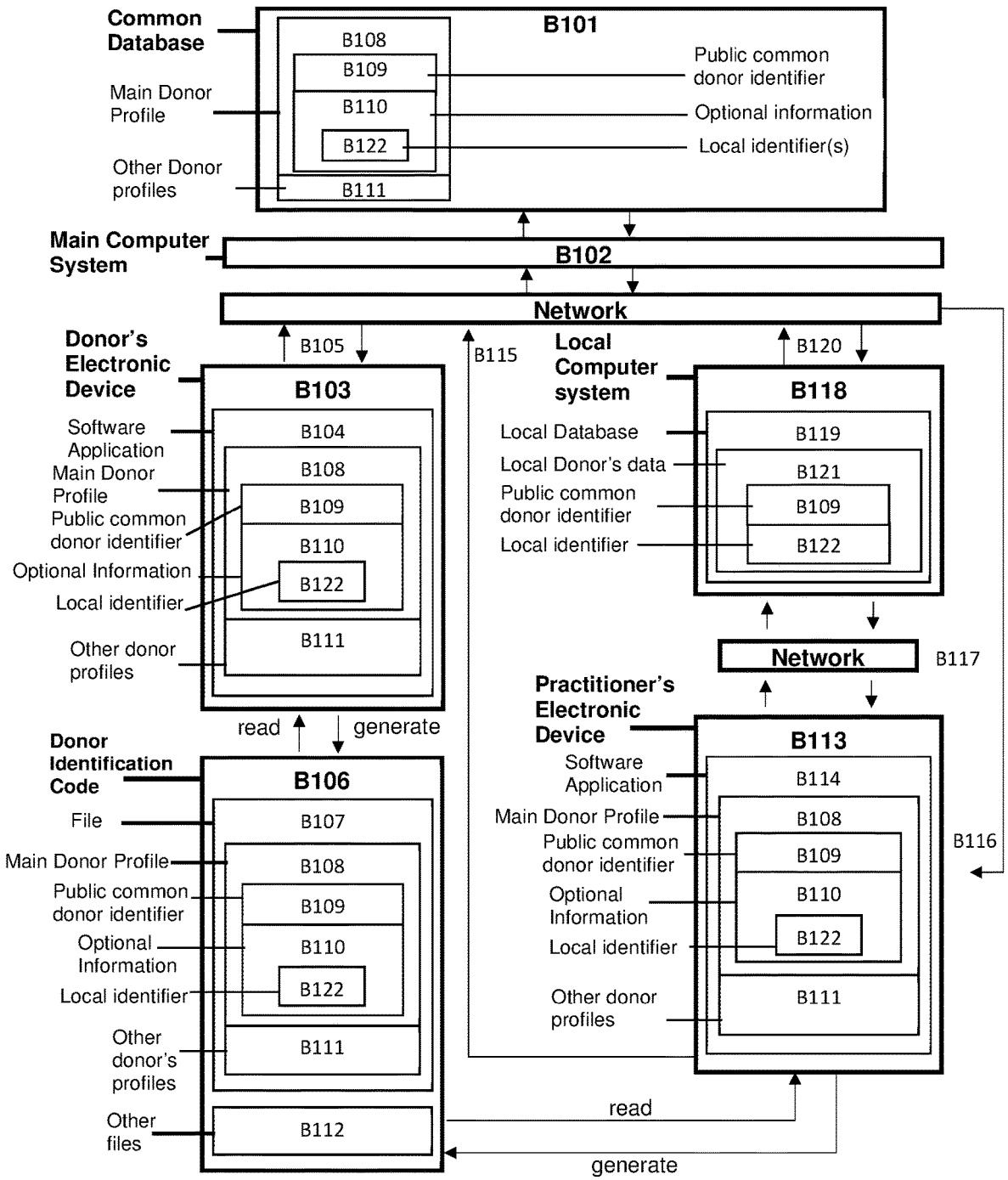
FIG. 2 illustrates the binary data communication of the donor information according to the invention.

The procedure of unified registration and identification of donors that the invention proposes, is configured, therefore, as a novelty within its field of application, since according to its implementation through a specific method the objectives outlined above are satisfactorily achieved, their characterizing details conveniently collected in the final claims accompanying the present specification.

Specifically, what the invention proposes, as indicated above, is a procedure for the registration and identification of donors developed with the aim of achieving the unification of the registration system and of the identification of the donors in distinct isolated donation facilities with different database systems (for example in a same territory or in several territories) and facilitate the exchange of information related to them even in offline mode (resilient system) and optionally using any type of binary data within a QR or NFC code (e.g. signed, encrypted and/or compressed), for cross-border identification and data access to donor information through different donation facilities, different electronic devices and computer systems using different software applications and database systems, and to improve the healthcare system, its safety, to save costs (for example, not allowing donations to previously excluded people in other donation facilities or with some detected diseases to save costs of extraction, handling, analysis, administration and destruction of biological products) and to allow the registration and traceability of donations even without connection to the network in natural disasters, virus attacks or terrorism.

For this, the method of the procedure comprises a first phase "A" to register a donor by themselves through a software application running in an electronic device with or without network connection (in online or offline modes), by a practitioner through a software application running in an electronic device (also in both online or offline modes) or being registered the donor automatically by the computer system of a center with network connection to a common database accessible by different electronic devices and computer systems of distinct donors and donation facilities through the main computer system. The second phase "B" is for the utilization of the binary data of the donor's identification code and of the data related to that donor in the common database, by means of a unique and non-transferable donor identification code (B106) for each donor in every center and/or computer system, which can be read (e.g. on the screen of the donor's electronic device or alternatively printed in the case of a broken device, among others) at a donation facility through the camera of an electronic device (both in online or offline modes) to access both the main donor profile (B108), the common public identifier (B109) of the donor and other data contained in the main donor profile (B108) or in other donor profiles (B111, 112) of the donor encrypted or not, such as the local donor identifier at that facility (if the donor also has a local donor identifier at that facility) and other data relevant to the donation procedure such as medical data. The method essentially comprises:

Generating a main donor profile (B108) and a common public identifier (B109) for the donor, carried out for example by a person (such as the donor themselves or a practitioner) through a software application (B104 or B114) running in an electronic device (B103 or B113) with or without network connection (B105, B115, B116, B120) or by a software service running in the computer system (B118) of a donation facility, associating the main donor profile (B108) with the common public identifier (B109) of the donor, deposited the main donor profile (B108) in a portable electronic device such as a mobile or tablet (B103 or B113) through a software application (B104 or B114), and storing the main donor profile both in a software application (B104 or B114) and in a common database (B101) accessible by the different centers by a computer system (B102), e.g. via REST API (Representational State Transfer Application Programming Interface), GraphQL (Graph Query Language) or gRPC (Google's Remote Procedure Call), among other possible.

Optionally, generating one or more local donor profiles (a different one for each distinct donation facility and with the local identifier of that facility for said individual or donor) and/or relevant medical donor profiles (B111) such as allergies, medications, medical interventions, illness (among others, such as the IPS and or USCDI specifications) and associated with the main donor profile (B108). This can be carried out, for example, by a person (such as the donor themselves or a practitioner) through a software application (B104 or B114) running in an electronic device (B103 or B113) or automatically by a software service running in the computer system (B118) of a donation facility, as an example, register a donor previously registered in the local database of the facility into the common database for the unified registry of donors of the invention). The other donor profiles (B111) are deposited in the software application (B104 or B114) used to generate the profiles and also in the common database (B101) after the generation of both the main donor profile (B108) and the public common donor identifier (B109). It must be noted than the common public identifier (B109) of the donor is generated when registering the donor in the donor database (carried out by the donor themselves, by a practitioner or automatically by the computer system in a center) can be also associated by each center with their local identifier (B122) in the local donor's data (B121) of the same individual in that center and stored in the local database (B119) of that center, carried out by a software application (B114) in a center with network connection to the computer system (B118) of that center or automatically by the computer system (B118) of a center, with a network connection (B120) to the main computer system, after registering a new donor in the common database (B101) through the main computer system (B102) of the invention, e.g. via REST API or gRPC, among others.

Generating a non-transferable identification code (B106) which contains within the same binary file (B107): the main donor profile (B108), the common public identifier (B109) of the donor, optional information (B110) of the donor in the main donor profile (B108) and optional information of the donor outside the main donor profile (B108) but in the same binary file (B107); optionally the identification code (B106) can also contain additional files (B112), e.g. JSON or XML files with medical data or other information of the donor in a secure way (e.g. through binary data encryption by using the binary data encoding in a QR code).

Identifying the donor by the system executed in the center through the identification code (B106) to which the main donor profile (B108), the common public identifier (B109) of the donor and other optional information (B110) including other donor profiles (B111 and B112) is associated to. If some information is contained in separate binary files within the identification code (B106 the software application of the practitioner attaches, internally, this information to the main donor profile (B108). Additionally, the software application (B104) of the donor can encrypt some data into the identification code (B106, e.g. by using symmetric or asymmetric encryption, generating a key pair for the donor and using DIDComm to establish a secure connection with the practitioner or healthcare service). Thus, the software application (B114) of the practitioner can optionally decrypt the identification code data (B106, e.g. using a DIDComm established connection). The identification code can be read by a software application through the camera installed in an electronic device and provides access to the personnel of the center to the binary data of the identification code (B106) of the donor such as the main donor profile (B108) and to other information stored in the identification code (B106, B109) and/or into the common database (B101) through a software application (B114). An audit object is generated by the software application (B114) of the practitioner every time an identification code is read (for audit purposes), the object containing at least both an identifier and a code with the result of the identification of the donor, additionally can contain an automatic donation exclusion detected (the time has not passed between donations, diseases detected, among others). This object is stored both within the software application (B114) of the practitioner, in the common database (B101) by sending it through the main computer system (B102), into the software application (B104) of the donor by sending it from the main computer system (B102) to the donor's application, and also into the computer system (B118) of the center by sending the software application (B114) of the practitioner said object to it, to alert both the donor and the corresponding personnel of this circumstance through a software application (B104, B114). After that, automatic updating of the donor information into the common database (B101) is carried out by the software application (B114) of the practitioner and/or by the computer system (B118) of the center, e.g. via REST API or gRPC, among other possible, for example to register information of the donation process (e.g. date of donation, hemoglobin test result, blood pressure, volume donated, place of donation, type of donation), among other data (such as tendency to suffer from dizziness, difficulty in donation for any reason, preferences of the donor when donating, without discarding others).

The non-transferable identification code (B106) created according to the invention method, which is unique and universal to identify univocally each individual (donor) across any donation facility with their main donor profile (B108), will be preferably generated on a portable electronic device such as a mobile phone or tablet (B103), among others, through a software application (B104) of the donor and after a donor biometric identification carried out by the electronic device (e.g. fingerprint, face recognition, among other possible). It must be noted that the main donor profile (B108), the common public identifier (B109) of the donor, optional information (B110) including other donor profiles (B111, B112) and the non-transferable identification code of the donor can be generated by the donor themselves even without a network connection (B105). For example, a person can create a main donor profile and related information to it through a software application (B104) running in an electronic device (B103) in offline mode; this data will be marked as offline by the software application to be synchronized with the common database through the main computer system when the network connection is recovered in the electronic device, carried out by the software application. The common public identifier of the donor will be unique and universal for each donor by using, as a non-limitative example, an UUID v4 format, so it can be generated in offline mode (a Version 4 UUID is a universally unique identifier that is generated using random numbers). When an internet connection is available, the information associated to the main donor profile (B108) can be stored both in the software application (B104) of the donor and in the common database (B101). So if a natural disaster has downed the internet connection or in the case of terrorism or a virus attack to one or more computer systems (B102, 118) and databases (B101, B119) the non-transferable identification code can be read in offline mode by a practitioner through a software application (B114) using the camera of the electronic device (B113), to access the donor data without any network connection to the computer system (B118) of the center, for example if no local area network (LAN) is available, and without connection to the main computer system, for example if a network connection (B115, B116) to Internet is not available. Once the network(s) connection(s) (B115, B116, B117) and/or the computer systems (B102, B118) and databases (B101, B119) are recovered, the software applications (B104, B114) of the donors, of the practitioners and of the computer systems (B118) of the donation facilities can synchronize the data with the common database (B101) through the main computer system (B102), e.g. via REST API or gRPC, among other possible. For example, the donor can fill in and sign a donation questionnaire of a center both in online and offline modes and also additional medical data can be filed or imported by the donor themselves (both in online and offline modes) and attached to the same file (B107) of the main donor profile (B108) or in separated files (B107 and B112) within the identification code (B106) generated through the software application (B104). In the same way, once a donation has been performed in the donation facility in offline mode, the software application of the practitioner can generate a QR or NFC code with the main donor profile and also containing the new data related to the donation performed, additionally can encrypt some data with the same key shared previously with the donor or generating a new encryption key to be communicated to the donor. In this manner the donor can read this identification code (a NFC tag, in the screen of an electronic device or printed, among others), generated by the software application of the practitioner in offline mode, by using the software application and the camera on their electronic device to incorporate the new data to their software application.

The identification of the donor is implemented, in a non-limitative manner, as the sum of a 2D matrix barcode in QR format or NFC code and donor's biometric data received by a sensor in an electronic device of both a donor, of a practitioner or of a center; the biometric data of the donor or the hash of that biometric data is stored both in a software application (e.g. the software application of the donor or of a practitioner), associated both to a specific electronic device and to a specific main donor profile, and sent to one or more computer systems (such as the computer system of a center if an electronic device of a center is used and to the main computer system to be stored in the common database and associated to a main donor profile); this biometric data is compared with the biometric data read through a software application (via fingerprint or facial recognition authentication, among others) in a electronic device with a biometric sensor before generating the identification code of the donor, as for example: a portable electronic device with an installed software application that reads the biometric signal of the donor to log the donor into that application and to show the QR code or bringing near the NFC code, which will be scanned/read by an electronic device of the donation facility; an electronic device of the donation facility that reads the biometric signal of the donor to show and print the donor QR code (e.g. when the donor arrives to the donation facility); a portable electronic device belonging to the donor showing the identification QR code or having a NFC code and an electronic device in the donation facility reading both the QR code of the donor's device or the NFC code and a biometric signal of the donor to verify the donor's identity.

Optionally, it also contemplates:

Capturing the results of the analysis sent automatically by the donation facility's computer system (B118) to the donor as recipient, storing them in the common database (B101) and notifying the donor when the results are available, for example through a software application (B104) installed in a portable electronic device (B103) of the individual or donor such as a mobile phone or tablet, among others.

Capturing relevant information from the computer system (B118) of other associated medical centers and incorporation of it into the common database (B101) via the main computer system (B102) by using REST API or gRPC, among others possible.

Detecting the presence of donors who can donate and who can be notified, for example depending on the donor information stored in the common database (B101) such as the date and type of the last donation, if the donor is excluded/or not from donating and the preferences of the donor in the system. By using geographical location of the donor on a portable electronic device (B103) such as a mobile phone, smart watch (among others), without ruling other possible (e.g. indoor positioning), and notify both to the donor via a software application (B104) and to the donation facility's computer system (B118) if the donor is a valid candidate to donate (e.g. via push notification or electronic message, among others).

Verifying the accuracy of the donor information in one or more computer systems (B118) of different centers (e.g. via REST API or gRPC, among others), and updating the results in the common database (B101) through the main computer system (B102).

As above mentioned, it should be noted that the code generated according to the method of the invention, which is unique and non-transferable for each donor, allows the donor to carry their medical information (and in a secure and resilient way) and, in a non-limitative manner, optionally consisting of a 2D matrix barcode in QR format (B106) that contains information, for example in one or more JSON data objects (B108, B109, B110, B111). The binary information of the 2D matrix barcode in QR format (B106) can also be optionally signed, encrypted and/or compressed, for example, in a zip file (B107); the identification code contains the main donor profile (B108) which has the common donor identifier (B109) associated to it and it will be the first JSON object in the identification code; the main donor profile (B108) contains the identifiers of the other donor profiles (B111, B112) with information of the donor. Optionally, the values of these identifiers can be the names of each file in the case that the identification code contains several files in a compressed file (B107). Additionally, the main donor profile (B108) can include all of some parts of the information of the donor stored in the common database (B101) as inline information (depending on the size of the information or on the preferences of the individual or donor).

It should be noted that the main donor profile and the common public identifier of the donor are generated either by the donor themselves through their electronic device (B103) with the software of the cited application (B104, B114) or one of the donation centers. It can also, through the application installed in any electronic device, and the software application (B104) generating the non-transferable code of the donor capture a biometric signal of the donor (for example to verify the identity of the donor before generating the unique and non-transferable code of that donor, for making a secure login into the software application or for signing data by this biometric signal).

With this, through the generation of the unique and non-transferable code (B106), the identification of the donor by the computer equipment or electronic device (B113), conveniently installed for that purpose in each center, can be made to access to the details of the main donor profile (B108) of each donor and to the information of the donor in the identification code (B106) and also in the common database (B101) if there is a network connection (B115, B116, B117), for example to validate the authenticity of the data of the donor. As a non-limitative example, the donor information in the common database (B101) contains the following information of the donor and some of this binary data can be included in the identification code (B106) for data portability: 1) main donor profile associated with the common public identifier of the donor, for example in UUID v4 format and with other profiles of the donor; 2) local donor profiles, such as identifiers from one or more different donation facilities; 3) personal profile with identification data of the individual (donor); 4) medical data profiles such as, in a non-limitative manner, blood typing (ABO group), previous donations made in any facility (the unified history of donations at any center), allergies, medications, previous health problems, without discarding others such as adverse reactions in previous donation processes, exclusions to donate, etc. (e.g. IPS or USCDI specifications); and 5) the above description is materialized into a 2D matrix barcode in QR format (B106) or NFC code in a non-limitative manner.

As explained above, the non-transferable identification code generated as both a 2D matrix barcode in QR format and NFC code, in a non-limitative manner, can carry both a public information type (not encrypted) and a second type of ciphered or encrypted information that will be accessible only to devices or personnel with the necessary permissions and decryption keys or passwords to decipher this information (e.g. medical information) through a software application.

In case of existence of any impediment to donate (the necessary time between donations has not passed, detected illness, . . . ), both the main computer system (B102), the computer system (B118) of the donation facility or an electronic device (B113) of some personnel in the donation facility (e.g., practitioner) with or without a network connection (B105) can detect it via the information of the donor, being able to generate an alarm (visual, sound) and/or an electronic message (push notification, email, SMS, among others) that alerts the corresponding personnel to this circumstance.

The generated code, in addition, can be static (always containing the same information, for example to be printed and used when the mobile device of the donor is broken or stolen) and/or dynamic; if dynamic (e.g. in the screen of a mobile device of the donor), the content of the code changes when the information it incorporates changes and, consequently, when the information of the donor in the common database (B101) accessible by the different centers is updated. As an example, when a new donation is registered for that donor in the common database (B101) through the main computer system (B102), carried out by the personnel at the donation facility through a software application (B114) in an electronic device (B113) after reading the code (B106) of the donor, and the data sent to the software application (B104) of the donor by the software (B114) of the personnel at the donation facility and/or by the computer system (B118) of the donation facility.

Optionally, the main computer system (B102) or the software application of the donor can capture new information of each donor, such as the results of laboratory analysis responsible for the creation of the same after each donation, and store the new information in the database (B101) accessible by the different centers. The code (B106) may incorporate all or part of said additional information that will be inserted into the donor's profile automatically by the main computer system (B102) in an automatic manner or by a method that is selective to a software application (e.g. carried out via REST API or gRPC, among others).

In addition, the software application (B114) in a donation facility may send an electronic notification to the donor, for example by email or by push notification to the software application (B104) in the donor's electronic device (B103) when new data of the donor is available (for example to be synchronized by the software application of the donor via REST API or gRPC, among others).

Optionally, the main computer system and the software application of the donor may capture relevant medical information from other associated medical centers, for example in case of detection of a disease in a routine blood analysis, and incorporate said data into information of the donor in the common database (B101) through the main computer system (B102) via REST API or gRPC, among others.

Also, optionally, both the software application of the donor itself and the information of the donor associated to the main donor profile (B108) and to the common public identifier (B109) of the donor allow to automatically detect the individual as a potential donor nearby at an active donation facility of any center (registered as donor in that center or not). At that time within a range of action, for example via geolocation through a software application (B104) in the mobile electronic device (B103) of the donor, a notification can be generated to the individual or donor indicating, via the software application (B104) of the donor in a mobile electronic device (B103), the possibility of donating blood in a nearby center (e.g. sending a push notification from the computer system to the software application of the mobile electronic device of the donor), but only if the donor is allowed to receive notifications to donate, for example via preferences stored in the software application (B104) and/or in the common database (B101), if the donor has not been excluded from donating, and if the donor has not reached the maximum number of annual donations according to the legislation of that specific territory.

If the information of the donor that incorporates the code (B106) has been generated by the donor themselves through the software application (B104) of the donor and then synchronized with the common database (B101) through the main computer system (B102), optionally, this computer system (B102) can verify that the information entered is authentic (e.g. checking the information with one or more external computer systems from one or more centers via API REST or gRPC, among others) and updating the information of that data as verified data in the common database (B101) accessible by all the centers.

In the procedure for global unified registration and universal identification of donors, the communication between the main computer system (B102) with the common database (B101), with the software application (B104) of the donors, with the different computer systems (B118) of each associated center and with the software application (B114) of the practitioner will be performed using HTTPS (Hypertext Transfer Protocol Secure), SSL (Secure Sockets Layer), TLS (Transport Layer Security), VPN (Virtual Private Network), without discarding others.

The described unified registration code and identification of donors consists, then, of an object of characteristics unknown until now for the purpose for which it is intended, reasons which, together with its practical utility, provide it with sufficient grounds to obtain the privilege of exclusivity that is requested.

In view of the described figures, and in accordance with the numeration adopted therein, it can be seen how the process comprises, essentially, the following phases and steps:

In a first phase A, the unified registry of donors comprises: i) generating a) a main donor profile, carried out by a person through a software application running in an electronic with or without network connection (such as the donor themselves or a practitioner) or by a software service running in the computer system of a center with network connection to a common database through the main computer system (accessible by the different electronic devices, centers and computer systems); if the main donor profile is generated by a person through a software application in an electronic device without network connection, the data is marked as offline by the software application to be synchronized with the common database of the invention when the network connection is recovered in the electronic device running the software application; b) one or more local donor profiles (a different one for each distinct donation facility and with the local identifier of that facility for said individual or donor) and/or relevant medical data profiles (e.g. IPS and/or USCDI specifications) and associated with the main donor profile, carried out both in online or offline modes by a person (such as the donor themselves or a practitioner) through a software application running in an electronic device or automatically by a software service running in the computer system of a donation facility with network connection to the common database (for example to register a donor previously registered in the local database of the facility into the common database); c) a common, unique and universal donor public identifier, generated by the software application both in online or offline modes using random numbers to identify univocally each individual (donor) across any center, associated with the main donor profile generated; additionally, the common public identifier of the donor can be associated by each center with their local identifier for the same individual in the local database of that center (e.g. carried out by a software application in a center with network connection to the computer system of that center or automatically by the computer system of that center after registering a new donor in the common database of the invention); and d) a personal and non-transferable identification code, for example in a 2D matrix barcode in binary mode, which contains within the same binary file: the main donor profile, the common public identifier of the donor, optional information of the donor in the main profile and optional information of the donor outside the main donor profile but in the same binary file; optionally the identification code can also contain additional files such as encrypted files with medical data or other donor information in a secure way (for example as encrypted data); ii) storing, in a software application (both in online and offline modes) and also in the common database if a network connection is available in the electronic device running the application (for example via REST API, GraphQL or gRPC) of the main donor profile, of the common public identifier of the donor, of additional profiles with other information of the donor and of the non-transferable identification code generated; and iii) automatically updating, by a computer system, the donor data and stored relevant medical data profiles with relevant health events and the date of the occurrence, after the registry of a donor in the common database.

After the first phase "A" is realized, the second phase "B" can be performed for the utilization of the unique and non-transferable identification code of the donor for cross border identification across distinct donation facilities, different electronic devices and computer systems using distinct software applications and database systems, comprising: iv) identifying the donor in a center, carried out by a software application both in online and offline modes by reading the personal and non-transferable identification code of the donor, implemented for example through a NFC code, 2D matrix barcode in QR format and binary mode in the screen of an electronic device of the donor or printed (among other possible), through the camera installed in an electronic device running a software application or by a NFC scanner, to read the data contained within the identification code of the donor with or without network connection to the computer system of a center via a local network connection or to the main computer system via the Internet (both in online or offline modes), to decode and/or to decipher (or decrypt) any binary data received in this way and to access to the main donor profile, to the public common donor identifier and to other optional donor information associated, carried out by authorized personnel and/or by a software application running in an electronic device at that center; v creating an audit object by the software application every time an identification code is read, containing this object at least an identifier and a code result of the identification of the donor and/or of an automatic donation exclusion detected (the time has not passed between donations, diseases detected, among others); storage of this object both in the software application that reads the identification code, in the common database by sending it through the main computer system, in the software application of the donor by sending it from the main computer system to the donor's application, and also in the computer system of the center by sending the application of the practitioner this object to it, to alert both the donor and the corresponding personnel of this circumstance through a software application; and vi) automatic updating of the donor information in the common database, carried out by the software application of the practitioner and/or by the computer system of a center (e.g. via REST API or gRPC, among other possible), for example to register information of the donation process (date of donation, hemoglobin test result, blood pressure, volume donated, place of donation, type of donation), among other data (such as tendency to suffer from dizziness, difficulty in donation for any reason, preferences of the donor when donating, without discarding others).

In addition, optionally, the procedure contemplates, in the use phase: vii) automatic capturing of information about the donor across distinct donation facilities and saving this information in the donor profile stored into the database accessible by the different centers, carried out by the main computer system (e.g. through API REST or gPRC, among others), which may include results of the donations, existence of adverse reaction after the donation, results of analytical or laboratory tests, among others; and viii) sending a notification to the donor when the new data of the donor is available (e.g. via push notification to the software application of the donor and/or by email), carried out by the main computer system (e.g. via API REST or gRPC, among other possible).

Optionally, the procedure also contemplates: ix) capturing relevant information of the same individual (donor) from other computer systems of distinct medical centers and database systems, carried out by the main computer system or by the software application of the donor themselves and then communicating this data to the main computer system (e.g. via REST API or gRPC, among others), which may include but not limited to collection of medical reports, radiological tests, allergological reports, emergency reports, previous detected diseases, detection of a disease in the blood test of the last donation made (FHIR resources or IPS documents); x) incorporating this information into the donor profile of the common database accessible by the different centers and register a global audit event in the common database after the detection of a serious illness in a donor or recipient of a donation, to carry out the appropriate actions (e.g. initiate protocols, check donations or traceability of the individual, temporary or definitive exemption from donation), carried out by the main computer system (e.g. via REST API or gGRPC, among others). xi) automatically detecting the presence of a donor in areas of endemic diseases or nearby at an active donation collection point at that time (registered as donor in that center or not), for example via geo location or indoor positioning through a software application in the mobile electronic device of the donor, carried out only if the donor has allowed it (e.g. via preferences stored in the software application and/or in the common database) and/or: if the donor has not been excluded from donating, if the donor has not reached the maximum number of annual donations according to the legislation of that specific territory and within a range of action; and xii) generating a notification to the individual (the potential donor) with the possibility of donating blood in a nearby center detected or the detection of a location of endemic diseases near to the donor (e.g. visual message in an electronic device through the software application of the donor, sending a push notification from the main computer system to the software application in the mobile electronic device of the donor) and update the donor information in the common database with the current date and location in the case of the detection of a nearby area of endemic diseases (e.g. via REST API or gRPC).

Finally, if the donor profile has been generated by the donor themselves through the software application of the donor, optionally the procedure contemplates: xiii) verifying the authenticity of the information of the donor stored in the common database (e.g. name, surname, blood group, identity document, donation made) carried out by the main computer system (e.g. checking the information with one or more external computer systems from one or more centers via API REST or gRPC, among others); and xiv) updating the donor information as verified data both in the common database (it may include but not limited to automatic system updating of donor information and automatic updating of the data by a laboratory or by a center through the main computer system) and in the software application of the donor (e.g. sending a notification to the donor via email or push notification to the software application in the mobile electronic device of the donor and updating the software application of the donor this information from the common database through the main computer system via REST API or GraphQL, among others).

Having sufficiently described the nature of the present invention, as well as the mode of putting it into practice, it is not considered necessary to make the explanation more extensive so that any expert in the field may understand its scope and the advantages that derive therefrom, stating that, within its essentiality, it may be carried out, in practice, in other modes of realization that differ in detail from that indicated by way of example, and to which it may equally reach the protection that is sought, provided that it is not altered, changed or modified in its fundamental principal.

What is claimed is:

1. A computer implemented method for a unified registry of donors having a global unified registration and a universal identification of donors, wherein the computer implemented method operates in online mode with a network connection, offline mode without the network connection, and both modes, the method comprising:

performing a first phase (A) at a main computer system and a common database to implement the unified registry of donors, wherein the main computer system and the common database are accessible by different electronic devices and computer systems of distinct centers, the first phase (A) comprising:

generating, at the main computer system and the common database, a main donor profile using, a software application running in an electronic device of the different electronic devices with or without the network connection or running in a computer system of the computer systems of the distinct centers, wherein upon the main donor profile being generated using the software application in the electronic device without the network connection, the data is marked as offline by the software application and synchronized with the common database when the network connection is recovered in the electronic device running the software application;

generating one or more local donor profiles on the computer system of the computer systems of the distinct centers, wherein the one or more local donor profiles are different and each of the one or more local donor profiles being associated with a local identifier of a facility for or a donor and/or relevant medical data profiles such as International Patient Summary (IPS) and/or United States Core Data for Interoperability (USCDI) specifications, and associated with the main donor profile, carried out both in the online or offline modes through the software application with the network connection to the common database to register the donor previously registered in a local database the facility into the common database;

generating a common, unique and universal donor public identifier using random numbers to identify univocally each individual donor across any center, carried out by the software application both in online or offline modes;

associating the common, unique and universal donor public identifier with the main donor profile of the donor;

associating, by the computer system, the common, unique and universal donor public identifier with the local identifier for the same donor in the local database with the network connection to update the local database and associate the public common donor identifier with the local identifier of the donor after registering the donor in the common database;

generating a personal and non-transferable identification code in a 2D matrix barcode in binary mode or in a NFC code, wherein the code comprises within the same binary file: the main donor profile, the common, unique and universal donor public identifier, optional information of the donor in the main profile and optional information of the donor outside the main donor profile but in the same binary file, wherein the identification code comprises additional encrypted files with medical data as encrypted data;

storing the personal and non-transferable identification code in the software application and also in the common database upon the network connection being available via Representational State Transfer Application Programming Interface (REST API), Graph Query Language (GraphQL) or Google's Remote Procedure Call (gRPC); and automatically updating, by the main computer system, via REST API or gRPC, the donor data and stored relevant medical data profiles in the common database with data of relevant health events and a date of the occurrence; and performing a second phase (B) to implement the universal identification of donors for cross border identification across the computer systems of the centers using the personal and non-transferable identification code, the second phase (B) comprising:

identifying the donor by reading the personal and non-transferable identification code of the donor, through a camera installed in an electronic device or a NFC scanner, to decode and/or to decipher any binary data received in this way and to access the main donor profile, the public common donor identifier and other optional donor information associated, or by reading the personal and non-transferable identification code of the donor, implemented through a Near Field Communication (NFC) code, a 2D matrix barcode in Quick Response (QR) format and binary mode after authentication of the donor in the main computer system, reading data contained within the personal and non-transferable identification code of the donor with or without the network connection;

creating an audit object in JavaScript Object Notation (JSON) format by the software application every time the personal and non-transferable identification code is read, wherein at least an identifier is automatically generated for the audit object and a code result of the identification of the donor and/or of an automatic donation exclusion detected;

storing of the audit object in the software application that reads the personal and non-transferable identification code, in the common database, and also in the computer system, generating and transmitting, by the main computer system, alerts for the electronic devices; and automatically updating if the network connection is available the donor information both in the common database and in the software application via push notification to the electronic devices and REST API, wherein the alerts share and register information of a donation in Fast Healthcare Interoperability Resources (FHIR) format including date, hemoglobin test result, blood pressure, place of donation, type of donation, volume donated, tendency to suffer from dizziness, difficulty in donation for any reason, and preferences of the donor when donating.

2. The method according to claim 1, wherein the identification code of a donor can be generated in offline mode without any network connection in the electronic device running the software application, wherein the donor is registered themselves or by the practitioner in offline mode by generating through a software application an universally unique identifier using random numbers including a Universally Unique Identifier (UUID) v4 identifier and any new data added or modified is marked as offline data by the software application to be synchronized with the common database through the main computer system when the network connection is recovered in the electronic device, carried out by the software application, wherein the software application of the practitioner can read in the identification code of the donor in a NFC tag in the screen of an electronic device of the donor or printed through the camera installed in an electronic device running a software application, wherein the software application of the practitioner is able to generate an identification code with both the common donor identifier and the main donor profile and also containing the new data related to a donation performed and the donor can read the identification code in a NFC tag, in the screen of an electronic device of the practitioner or printed generated by the software application of the practitioner in offline mode, by using a NFC scanner the software application and the camera on their electronic device, and wherein the software application of the donor is able to read in offline mode that identification code generated by the software application of the practitioner to incorporate in this way the new data of the donor in FHIR format into the donor software application.

3. The method according to claim 1, wherein the identification code is generated after a biometric identification of the individual through a biometric sensor installed in an electronic device of both a donor, of a practitioner or of a center and through a software application via fingerprint or facial recognition authentication, among others and biometric data of the donor is used to generate encryption and/or sign keys including public and private key pairs in asymmetric encryption scheme and generating a Decentralized Identifier (DID) Document of the donor with the public keys, to decrypt some encrypted data of that donor including encrypted data in the identification code and to validate the data of a donor including signed data in the identification code, wherein the keys generated through biometric data by a software application through the biometric data obtained by a biometric sensor of the donor in an electronic device are stored securely on the electronic device of the donor in a secure storage of a smartphone, wherein the public keys generated is sent to the main computer system and stored in the common database in a DID Document associated with the donor's main profile; when the donor wishes to authenticate in the main computer system and/or in their software application through a biometric sensor in an electronic device including in the software application of the donor and with the main computer system, wherein the donor is prompted by biometrics in the electronic device through their software application which unlocks the securely stored private key and a cryptographic signature is generated by this software application, sent to the computer system and verified to authorize the donor in the software application and in the main computer system.

4. The method according to claim 1, further comprising: automatically capturing information about the donor across distinct donation facilities and saving this information in the software application of the donor and in the donor profile stored into the common database accessible by the different centers, carried out by the main computer system through API REST or gPRC, which may include FHIR resources and IPS documents with results of the donations, history of donations, existence of adverse reaction after the donation, results of analytical or laboratory tests;

sending a notification to a donor's electronic device when the donation process is consultable;

capturing relevant information of the same individual donor from other computer systems of distinct medical centers and database systems, carried out by the main computer system or by the software application of the donor themselves and then communicating this data to the main computer system via REST API or gRPC, which may include a collection of medical reports, radiological tests, allergological reports, emergency reports, previous detected diseases, detection of a disease in the blood test of the last donation made in FHIR resources and IPS documents; and incorporating the information into the donor profile of the common database accessible by the different centers and register a global audit event in the common database after the detection of a serious illness in a donor or recipient of a donation, to carry out the appropriate actions including initiating protocols, check donations or traceability of the individual, temporary or definitive exemption from donation, carried out by the main computer system via REST API or gRPC.

5. The method according to claim 1, further comprising: detecting the presence of a registered or unregistered donor in areas of endemic diseases or nearby an active donation collection point at that time via geo location or indoor positioning through a software application in the mobile electronic device of the donor, carried out only if the donor has allowed it via preferences stored in the software application and/or in the common database and/or if the donor has not been excluded from donating, if the donor has not reached the maximum number of annual donations according to the legislation of that specific territory and within a range of action; and generating a notification to a potential donor individual with the possibility of donating in a nearby center detected or the detection of a location of endemic diseases close to the donor via visual message in an electronic device through the software application of the donor, sending a push notification from the main computer system to the software application in the mobile electronic device of the donor and update the donor information in the common database with the current date and location in the case of the detection of a nearby area of endemic diseases via REST API.

6. The method according to claim 1, wherein when the profile of donor has been generated by the user, the procedure further comprising:

automatic system verifying of the authenticity of the information of the donor stored in the common database including FHIR resources, IPS document and USCDI classification of FHIR resources carried out by the main computer system by checking the information with one or more external computer systems from one or more centers via API REST or gRPC; and automatic system updating of the donor information as verified data both in the common database which includes automatic system updating of donor information and automatic updating of the data by a laboratory or by a center through the main computer system, and in the software application of the donor via sending a notification to the donor via email or push notification to the software application in the donor's mobile electronic device and updating the software application of the donor this information from the common database through the main computer system via REST API or GraphQL.

7. The method according to claim 1, wherein the non-transferable identification code contains binary information including FHIR resources and/or an IPS document in a NFC code or 2D matrix barcode in QR format and is signed, encrypted and/or compressed, the identification code containing the main donor profile, which has the common donor identifier associated to it, and the main donor profile contains the identifiers of the other profiles with information of the donor and the values of these identifiers are optionally the names of each file in the case that the identification code contains several files in a compressed file, and wherein the main profile can include all or some parts of the donor's information stored in the common database depending on the size of the information or on the preferences of the individual or donor as inline information, the identifiers of the other profiles of the donor are stored as UUID v4, the local donor profiles containing the local identifier of the same individual in other facilities, some medical data can be marked as relevant by the practitioners or by the donor themselves and the medical data can be stored as private data in the identification code, the identification code having additional digital signatures of the data contained in the identification code.

8. The method according to claim 1, wherein to share medical data of the donor within the identification code which includes the donor sharing some or all medical information in FHIR and IPS formats with a practitioner in offline mode before performing the donation or the practitioner sharing with a donor the result of a donation once it has been completed, the software application generating the identification code can encrypt and sign the data containing FHIR resources through symmetric and/or asymmetric cryptography and can send the information using the DIDcomm specification to establish a secure connection and to decrypt and verify the information.

9. A computer system for a unified registry of donors having a global unified registration and universal identification of donors, wherein the computer system operates in online mode with a network connection, offline mode without the network connection, and both modes, wherein the computer system is distributed across one or more territories for cross border identification of a donor across different electronic devices and computer systems of centers having different software applications and different local database systems; wherein the system comprises:

a main computer system and a common database, the main computer system accessible by the different electronic devices and computer systems of the centers, the main computer system providing the unified registry of donors;

wherein the main computer system generates:

a main donor profile by a software application running in an electronic device of the different electronic device with or without the network connection or running in a computer system of the computer systems, wherein upon the main donor profile being generated by the software application in the electronic device without the network connection, the data is marked as offline by the software application and synchronized with the common database when the network connection is recovered in the electronic device running the software application;

one or more local donor profiles on the computer system of a center, wherein the one or more local donor profiles are different and each of the one or more local donor profiles being associated with a local identifier of a facility for a donor and/or relevant medical data profiles such as International Patient Summary (IPS) and/or United States Core Data for Interoperability (USCDI) specifications, and associated with the main donor profile, carried out both in the online or offline modes through the software application with the network connection to the common database to register the donor previously registered in a local database of the facility into the common database;

a common, unique and universal donor public identifier using random numbers to identify univocally each individual donor across any center, carried out by the software application both in online or offline modes;

wherein the common database associates the common, unique and universal donor public identifier with the main donor profile of the donor, and wherein the computer system associates the common, unique and universal donor public identifier with the local identifier for the donor in the local database after registering the donor in the common database;

wherein the main computer system generates a personal and non-transferable identification code in a 2D matrix barcode in binary mode or in a NFC code, wherein the code comprises within the same binary file: the main donor profile, the common, unique and universal donor public identifier, optional information of the donor in the main profile and optional information of the donor outside the main donor profile but in the same binary file, wherein the identification code comprises additional encrypted files with medical data as encrypted data;

wherein the main computer system stores the main donor profile, the common, unique and universal donor public identifier, additional profiles with other information of the donor and of the non-transferable identification code generated; and wherein the main computer system automatically updates the donor data and stored relevant medical data profiles in the common database with relevant health events and a date of the occurrence; and wherein the computer system identifies the donor by reading the personal and non-transferable identification code of the donor, through a camera installed in an electronic device or a NFC scanner, to decode and/or to decipher any binary data received in this way and to access the main donor profile, the public common donor identifier and other optional donor information associated, wherein the computer system reads the personal and non-transferable identification code of the donor, implemented through a Near Field Communication (NFC) code, a 2D matrix barcode in Quick Response (QR) format and binary mode after authentication of the donor in the main computer system, wherein the computer system reads data contained within the personal and non-transferable identification code of the donor with or without the network connection;

wherein the computer system creates an audit object in JavaScript Object Notation (JSON) format by the software application every time the personal and non-transferable identification code is read, wherein at least an identifier is automatically generated for the audit object and a code result of the identification of the donor and/or of an automatic donation exclusion;

wherein the computer system stores the audit object both in the software application that reads the identification code and in the common database by sending it through the main computer system;

wherein the main computer system generates and transmit alerts for the electronic devices; and automatically updates if the network connection is available the donor information both in the common database and in the software application via push notification to the electronic devices and REST API, wherein the alerts share and register information of a donation in Fast Healthcare Interoperability Resources (FHIR) format including date, hemoglobin test result, blood pressure, place of donation, type of donation, volume donated, tendency to suffer from dizziness, difficulty in donation for any reason, and preferences of the donor when donating.

* * * * *